(12) United States Patent
Li et al.

(10) Patent No.: US 9,321,857 B2
(45) Date of Patent: Apr. 26, 2016

(54) CARRIER FOR OLEFIN POLYMERIZATION CATALYST, PREPARATION METHOD AND APPLICATION THEREOF

(75) Inventors: Weili Li, Beijing (CN); Xianzhi Xia, Beijing (CN); Yuexiang Liu, Beijing (CN); Jigui Zhang, Beijing (CN); Suzhen Qiao, Beijing (CN); Jin Zhao, Beijing (CN); Ping Gao, Beijing (CN); Xinsheng Wang, Beijing (CN); Yang Tan, Beijing (CN); Zhihui Zhang, Beijing (CN); Linna Yang, Beijing (CN); Ruilin Duan, Beijing (CN); Renqi Peng, Beijing (CN)

(73) Assignees: China Petroleum & Chemical Corporation, Beijing (CN); Beijing Research Institute of Chemical Industry, China Petroleum & Chemical Corporation, Beijing (CN)

( * ) Notice: Subject to any disclaimer, the term of this patent is extended or adjusted under 35 U.S.C. 154(b) by 974 days.

(21) Appl. No.: 13/501,850

(22) PCT Filed: Oct. 18, 2010

(86) PCT No.: PCT/CN2010/001632
§ 371 (c)(1),
(2), (4) Date: Jun. 28, 2012

(87) PCT Pub. No.: WO2011/044761
PCT Pub. Date: Apr. 21, 2011

(65) Prior Publication Data
US 2012/0264590 A1     Oct. 18, 2012

(30) Foreign Application Priority Data

Oct. 16, 2009  (CN) ............... 2009 1 0235562
Oct. 16, 2009  (CN) ............... 2009 1 0235563
Oct. 16, 2009  (CN) ............... 2009 1 0235564
Oct. 16, 2009  (CN) ............... 2009 1 0235565

(51) Int. Cl.
*B01J 21/00*     (2006.01)
*B01J 23/00*     (2006.01)
(Continued)

(52) U.S. Cl.
CPC ............. *C08F 10/00* (2013.01); *C07F 3/003* (2013.01); *C08F 110/06* (2013.01)

(58) Field of Classification Search
USPC .................... 502/102, 100, 150, 169, 172
See application file for complete search history.

(56) References Cited

U.S. PATENT DOCUMENTS 4,399,054 A    8/1983  Ferraris et al.
4,421,674 A    12/1983  Invernizzi et al.
(Continued)

FOREIGN PATENT DOCUMENTS

CN    1016422 B    4/1992
CN    1020448 C    5/1993
(Continued)

OTHER PUBLICATIONS

International Search Report for International Patent Application No. PCT/CN2010/001632, mailed Jan. 13, 2011.
(Continued)

*Primary Examiner* — James McDonough
(74) *Attorney, Agent, or Firm* — Finnegan, Henderson, Farabow, Garrett & Dunner, LLP

(57) ABSTRACT

A spheric magnesium compound comprises a reaction product of at least the following components: (a) a magnesium halide having a formula of $MgX_{2-n}R_n$, wherein X is independently chloride or bromide, R is a $C_1$-$C_{14}$ alkyl, a $C_6$-$C_{14}$ aryl, a $C_1$-$C_{14}$ alkoxy, or a $C_6$-$C_{14}$ aryloxy, and n is 0 or 1; (b) an alcohol compound; and (c) an epoxy compound having a general formula (I), wherein $R_2$ and $R_3$ are independently hydrogen, a $C_1$-$C_5$ linear or branched alkyl, or a $C_1$-$C_5$ linear or branched haloalkyl. The magnesium compound has characteristic DSC curve and X-ray diffraction pattern, and can be used as a carrier for olefin polymerization catalyst.

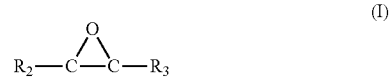

(I)

stereoregularity of polymer having high melt index, and low content of polymer fines.

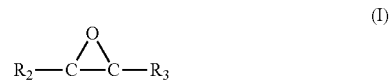

(I)

20 Claims, 3 Drawing Sheets

(51) Int. Cl.
  *B01J 25/00* (2006.01)
  *B01J 29/00* (2006.01)
  *B01J 31/00* (2006.01)
  *C08F 10/00* (2006.01)
  *C07F 3/00* (2006.01)
  *C08F 110/06* (2006.01)

(56) References Cited

U.S. PATENT DOCUMENTS

| | | | |
|---|---|---|---|
| 4,469,648 A | 9/1984 | Ferraris et al. | |
| 4,727,051 A | 2/1988 | Breen et al. | |
| 5,006,499 A | 4/1991 | Daire | |
| 5,034,361 A | 7/1991 | Job et al. | |
| 5,100,849 A | 3/1992 | Miya et al. | |
| 5,817,591 A | 10/1998 | Shamshoum et al. | |
| 5,849,655 A | 12/1998 | Shamshoum et al. | |
| 6,020,279 A | 2/2000 | Uwai et al. | |
| 6,127,304 A | 10/2000 | Sacchetti et al. | |
| 6,323,152 B1 | 11/2001 | Sacchetti et al. | |
| 6,365,540 B1 | 4/2002 | Garoff et al. | |
| 6,617,278 B1 * | 9/2003 | Jin | C08F 10/00 502/111 |
| 7,060,763 B2 | 6/2006 | Evangelisti et al. | |
| 7,087,688 B2 | 8/2006 | Evangelisti et al. | |
| 7,153,804 B2 * | 12/2006 | Chen | C08F 10/00 502/102 |
| 7,307,035 B2 | 12/2007 | Sacchetti et al. | |
| 7,332,455 B2 | 2/2008 | Wei et al. | |
| 7,388,061 B2 | 6/2008 | Gao et al. | |
| 7,566,676 B2 | 7/2009 | Yang et al. | |
| 2001/0039241 A1 | 11/2001 | Job | |
| 2004/0229748 A1 * | 11/2004 | Chen | C08F 10/06 502/118 |
| 2005/0209097 A1 | 9/2005 | Yang et al. | |
| 2005/0227858 A1 * | 10/2005 | Chen | C08F 10/00 502/103 |
| 2005/0239636 A1 | 10/2005 | Gao et al. | |
| 2006/0025300 A1 | 2/2006 | Diego et al. | |
| 2006/0287446 A1 * | 12/2006 | Gao | C08F 10/00 526/124.3 |
| 2008/0262178 A1 | 10/2008 | Grun et al. | |
| 2008/0293897 A1 | 11/2008 | Collina et al. | |
| 2009/0182103 A1 | 7/2009 | Chang et al. | |
| 2009/0281259 A1 | 11/2009 | Park et al. | |

FOREIGN PATENT DOCUMENTS

| | | |
|---|---|---|
| CN | 1091748 A | 9/1994 |
| CN | 1141285 A | 1/1997 |
| CN | 1034736 C | 4/1997 |
| CN | 1436796 A | 8/2003 |
| CN | 1453298 A | 11/2003 |
| CN | 1463990 A | 12/2003 |
| CN | 1480469 A | 3/2004 |
| CN | 1177868 C | 12/2004 |
| CN | 1551893 A | 12/2004 |
| CN | 1580136 A | 2/2005 |
| CN | 1590415 A | 3/2005 |
| CN | 1610704 A | 4/2005 |
| CN | 1611516 A | 5/2005 |
| CN | 1611517 A | 5/2005 |
| CN | 1617893 A | 5/2005 |
| CN | 1726080 A | 1/2006 |
| CN | 1255436 C | 5/2006 |
| CN | 1834118 A | 9/2006 |
| CN | 1875038 A | 12/2006 |
| CN | 1898278 A | 1/2007 |
| CN | 1922212 A | 2/2007 |
| CN | 1948352 A | 4/2007 |
| CN | 101056894 A | 10/2007 |
| CN | 100348624 C | 11/2007 |
| CN | 101190953 A | 6/2008 |
| CN | 101421316 A | 4/2009 |
| EP | 0361493 A1 | 4/1990 |
| EP | 0395083 A2 | 10/1990 |
| EP | 0700936 A1 | 3/1996 |
| EP | 0728724 A1 | 8/1996 |
| JP | 59210906 A | 11/1984 |
| JP | 2002-506893 | 3/2002 |
| JP | 2005-517746 | 6/2005 |
| JP | 2006-523730 | 10/2006 |
| JP | 2007-505955 | 3/2007 |
| JP | 2007-532723 | 11/2007 |
| KR | 10-2006-0013486 | 2/2006 |
| WO | WO 87/07620 | 12/1987 |
| WO | WO 93/11166 | 6/1993 |
| WO | WO 98/44009 | 10/1998 |
| WO | WO 03/068723 A1 | 8/2003 |
| WO | WO 03/068828 A1 | 8/2003 |
| WO | WO 03/082930 A2 | 10/2003 |
| WO | WO 2004/026920 A1 | 4/2004 |
| WO | WO 2009/080568 A2 | 7/2009 |

OTHER PUBLICATIONS

English language Abstract of CN 101190953A dated Jun. 4, 2008.
English language Abstract of CN 1091748A dated Sep. 7, 1994.
English language Abstract of CN 1110281A dated Oct. 18, 1995.
English language Abstract of CN 1463990A dated Dec. 31, 2003.
English language Abstract of CN 1480469A dated Mar. 10, 2004.
English language Abstract of CN 1590415A dated Mar. 9, 2005.
English language Abstract of JP 59210906A dated Nov. 29, 1984.
Office Action for U.S. Appl. No. 13/501,585, mailed Jan. 15, 2013.
Response to Restriction Requirement for U.S. Appl. No. 13/501,585, filed Feb. 15, 2013.
Office Action for U.S. Appl. No. 13/501,585, mailed Apr. 2, 2013.
Amendment and Response to Office Action for U.S. Appl. No. 13/501,585, filed Jul. 2, 2013.
Final Office Action for U.S. Appl. No. 13/501,585, mailed Aug. 14, 2013.
Reply to Final Office Action under 37 C.F.R. § 1.114 for U.S. Appl. No. 13/501,585, filed Dec. 16, 2013.
Office Action for U.S. Appl. No. 13/501,585, mailed Jul. 28, 2014.
Reply to Office Action under 37 C.F.R. § 1.114 for U.S. Appl. No. 13/501,585, filed Jan. 28, 2015.
Final Office Action for U.S. Appl. No. 13/501,585, mailed Apr. 17, 2015.
Reply to Final Office Action for U.S. Appl. No. 13/501,585, filed Jul. 17, 2015.
Notice of Allowance and Fees Due for U.S. Appl. No. 13/501,585, mailed Sep. 30, 2015.
International Search Report for International Patent Application No. PCT/CN2010/001631 mailed Jan. 20, 2011.

* cited by examiner

CARRIER FOR OLEFIN POLYMERIZATION CATALYST, PREPARATION METHOD AND APPLICATION THEREOF

CROSS REFERENCE OF RELATED APPLICATIONS

The present application claims the benefit of the Chinese Patent Application Nos. 200910235562.3, 200910235563.8, 200910235564.2 and CN200910235565.7, filed on Oct. 16, 2009, which are incorporated herein by reference in their entirety and for all purposes.

FIELD OF THE INVENTION

The present invention relates to a carrier useful in the preparation of catalyst components for olefin polymerization, a method for the preparation thereof and application thereof. More specifically, the present invention relates to a novel spheric magnesium compound carrier obtained by reacting a magnesium halide-alcohol adduct solution with an epoxy compound, a method for the preparation thereof and application thereof.

BACKGROUND ART

Active magnesium halide carriers useful in the preparation of catalyst components for olefin polymerization are well known in the art. A usual active magnesium halide carrier is an adduct of a magnesium halide and an alcohol, generally in the form of spheric particles. Spheric catalyst components are obtained by reacting the magnesium halide-alcohol adduct carrier with a titanium compound, such as a titanium halide, and an electron donor compound. When used in olefin polymerization, in particular in propylene polymerization, such catalyst components exhibit high polymerization activities and high stereospecificities, and the resulting polymers have good particle morphology.

The disclosed magnesium halide-alcohol adduct carriers comprise generally only magnesium dichloride and an alcohol. Some of the disclosed magnesium halide-alcohol adduct carriers further comprise a minor amount of water. Such magnesium halide-alcohol adduct carriers may be prepared by known processes, such as spray drying process, spray cooling process, high-pressure extruding process, or high speed stirring process. See, for example, U.S. Pat. No. 4,421,674, U.S. Pat. No. 4,469,648, WO 08707620, WO 9311166, U.S. Pat. No. 5,100,849, U.S. Pat. No. 6,020,279, U.S. Pat. No. 4,399,054, EP 0395083, EP-A-700936, CN 1034736, CN 1463990, CN 1580136, U.S. Pat. No. 6,127,304 and U.S. Pat. No. 6,323,152.

WO98/44009 discloses an adduct of formula $MgCl_2 \cdot mROH \cdot nH_2O$, wherein R is a $C_1$-$C_{10}$ alkyl, $2 \leq m \leq 4.2$, and $0 \leq n \leq 0.7$. The X-ray diffraction pattern of the adduct is characterized in that, in the range of 2θ diffraction angles between 5° and 15°, there are three main diffraction lines at diffraction angle 2θ of 8.8±0.2°, 9.4±0.2° and 9.8±0.2°, the intensest diffraction line being the one at 2θ of 8.8±0.2°, the intensity of the other two diffraction lines being at least 0.2 times the intensity of the intensest diffraction line. Besides the above-described X-ray diffraction pattern, the above adduct is further characterized by its differential scanning calorimetry (DSC) profile, in which no peaks are present at temperatures below 90° C. or, even if peaks are present below said temperature, the fusion enthalpy associated with said peaks is less than 30% of the total fusion enthalpy.

WO2003/082930 discloses an adduct of formula $MgCl_2 \cdot mEtOH$, wherein $2.5 \leq m \leq 3.2$. The adduct optionally contains water up to 1 wt % based on the total weight of the adduct. The X-ray diffraction pattern of the adduct is characterized in that, in the range of 2θ diffraction angles between 5° and 15°, there are three main diffraction lines at diffraction angle 2θ of 8.8±0.2°, 9.4±0.2° and 9.8±0.2°, the intensest diffraction line being the one at 2θ of 8.8±0.2°, the intensity of the other two diffraction lines being at least 0.2 times the intensity of the intensest diffraction line. The DSC profile of the adduct is characterized by a highest melting temperature peak over 109° C. and an associated fusion enthalpy of 103 J/g or lower.

WO2004/026920 discloses an adduct of formula $MgCl_2 \cdot mEtOH \cdot nH_2O$, wherein $3.4 \leq m \leq 4.4$, and $0 \leq n \leq 0.7$. The X-ray diffraction pattern of the adduct is characterized in that, in the range of 2θ diffraction angles between 5° and 10°, there are at least two diffraction lines at 2θ of 9.3±0.2° and 9.9±0.2°, the intensest diffraction line being the one at 2θ of 9.3±0.2°, the intensity of the other diffraction line being lower than 0.4 times the intensity of the intensest diffraction line. The DSC profile of the adduct is characterized in that there is only one melting peak in a range of from 90 to 105° C.

Besides the above-mentioned magnesium halide-alcohol binary adduct carriers, the prior art also discloses other forms of active magnesium halide carriers. For example, CN1922212A discloses a carrier obtained by reacting a solution of a magnesium halide in a cyclic ether and an alcohol with a titanium halide. CN101190953A discloses a magnesium-containing adduct carrier formed by reacting a $C_1$-$C_5$ alcohol with powdery magnesium in the presence of a methyl halide. CN1590415A discloses a complex carrier prepared by reacting a $C_2$-$C_4$ lower alcohol with powdery magnesium in the presence of a methyl halide to form a homogeneous magnesium compound solution and supporting the formed magnesium compound on a spheric silica carrier. CN1016422B, CN1177868C, CN101056894A, U.S. Pat. No. 4,727,051, CN1255436C, U.S. Pat. No. 5,034,361, U.S. Pat. No. 5,849,655, U.S. Pat. No. 5,817,591 and U.S. Pat. No. 4,469,648 disclose active magnesium dichloride carriers prepared by using an alkoxy magnesium as a starting material.

SUMMARY OF THE INVENTION

After diligently studying, the inventors have found that a novel spheric magnesium compound can be obtained by reacting a magnesium halide-alcohol adduct solution with an epoxy compound. The spheric magnesium compound has a DSC profile and an X-ray diffraction pattern different from those of known magnesium dichloride-alcohol adduct carriers and magnesium dichloride carriers. The spheric magnesium compound may be used as a carrier to react with a titanium compound and an optional internal electron donor, thereby providing a spheric catalyst component for olefin polymerization with desired performance. On this basis, the present invention was made.

An object of the invention is to provide a novel spheric magnesium compound useful as a carrier used in the preparation of a catalyst component for olefin polymerization, comprising a reaction product of at least the following components: (a) a magnesium halide as defined hereinbelow; (b) an alcohol compound; and (c) an epoxy compound as defined hereinbelow.

Another object of the invention is to provide a novel spheric magnesium compound useful as a carrier used in the preparation of a catalyst component for olefin polymerization, having a characteristic DSC profile.

Another object of the invention is to provide a novel spheric magnesium compound useful as a carrier used in the preparation of a catalyst component for olefin polymerization, having a characteristic X-ray diffraction pattern.

Another object of the invention is to provide a process for preparing the spheric magnesium compound according to the invention.

Another object of the invention is to provide use of the spheric magnesium compound according to the invention as a carrier in the preparation of a catalyst component for olefin polymerization.

The spheric magnesium compound useful as a carrier used in the preparation of a catalyst component for olefin polymerization has a good particle morphology and narrow particle size distribution, and the process for the preparation thereof is simple and feasible, and consumes less energy. When used in olefin polymerization, in particular in propylene (co)polymerization, the solid catalyst component prepared by using said compound as a carrier achieves at least one of the following desired effects: high polymerization activity of catalyst, high stereospecificity of catalyst, good hydrogen response of catalyst, high stereoregularity of polymer having high melt index, and low content of polymer fines.

DETAILED DESCRIPTION OF THE PREFERRED EMBODIMENTS

Figure 1:
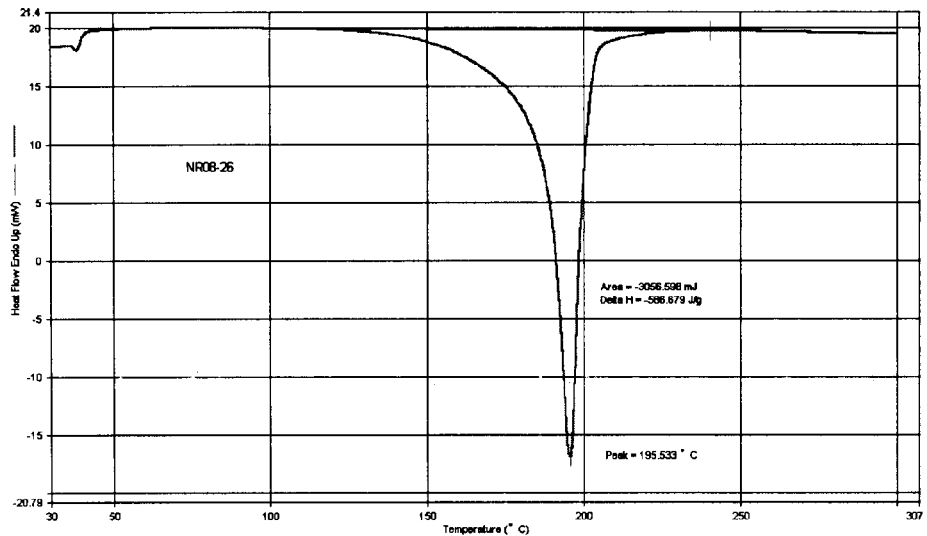
FIG. 1 shows a DSC profile of the magnesium compound carrier prepared in Example 1.

As used herein, the term "catalyst component" intends to mean main catalyst component or procatalyst, which, together with a conventional cocatalyst such as an alkyl aluminum compound and an optional external electron donor, constitutes a catalyst for olefin polymerization.

As used herein, the term "spheric magnesium compound" or "spheric carrier" means that the magnesium compound or carrier has a spheroid-like particle morphology, but does not require that the particles of the magnesium compound or carrier are in the form of perfect spheroid. Similarly, as used herein, the term "spheric catalyst component" means that the catalyst component has a spheroid-like particle morphology, but does not require that the particles of the catalyst component are in the form of perfect spheroid.

In a first aspect, the present invention provides a magnesium compound useful as a spheric carrier used in the preparation of a catalyst component for olefin polymerization, the magnesium compound comprising a reaction product of at least the following components:

(a) a magnesium halide represented by a general formula of $MgX_{2-n}R_n$, wherein X is independently chloride or bromide, R is a $C_1$-$C_{14}$ alkyl, a $C_6$-$C_{14}$ aryl, a $C_1$-$C_{14}$ alkoxy, or a $C_6$-$C_{14}$ aryloxy, and n is 0 or 1;

(b) an alcohol compound, preferably an alcohol compound represented by a general formula of $R_1OH$, wherein $R_1$ is a $C_1$-$C_{12}$ alkyl, a $C_3$-$C_{10}$ cycloalkyl, a $C_7$-$C_{12}$ aralkyl or a $C_6$-$C_{10}$ aryl, and preferably a $C_1$-$C_8$ alkyl; and (c) an epoxy compound represented by a general formula (I):

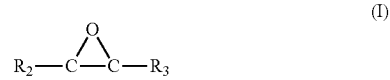

(I)

wherein $R_2$ and $R_3$ are independently hydrogen, a $C_1$-$C_5$ linear or branched alkyl, or a $C_1$-$C_5$ linear or branched haloalkyl, and preferably hydrogen, a $C_1$-$C_3$ alkyl or a $C_1$-$C_3$ haloalkyl.

Examples of the magnesium halide compound of the general formula $MgX_{2-n}R_n$ include, but are not limited to, magnesium dichloride, magnesium dibromide, phenoxy magnesium chloride, isopropoxy magnesium chloride, and butoxy magnesium chloride, with magnesium dichloride being preferred. The magnesium halides may be used alone or in combination.

The alcohol compound is preferably ones of the general formula of $R_1OH$, wherein $R_1$ is a $C_1$-$C_{12}$ alkyl, a $C_3$-$C_{10}$ cycloalkyl, a $C_7$-$C_{12}$ aralkyl or a $C_6$-$C_{10}$ aryl, and preferably a $C_1$-$C_8$ alkyl. The alcohol compound can also be glycols. Examples of the alcohol compound useful in the invention include, but are not limited to, methanol, ethanol, propanol, isopropanol, n-butanol, isobutanol, pentanol, isopentanol, n-hexanol, n-octanol, 2-ethylhexanol, ethylene glycol and propylene glycol. The alcohol compounds may be used alone or in combination.

Examples of the epoxy compound of the general formula (I) include, but are not limited to, epoxy ethane, epoxy propane, epoxy butane, epoxy chloropropane, epoxy chlorobutane, epoxy bromopropane, and epoxy bromobutane. The epoxy compounds may be used alone or in combination.

In the formation of the spheric magnesium compound, relative to one mole of the magnesium halide, the amount of the alcohol compound used may range from 4 to 40 moles, preferably from 4 to 30 moles, more preferably from 6 to 25 moles, and still more preferably from 6 to 20 moles, and the amount of the epoxy compound used may range from 1 to 10 moles, and preferably from 2 to 6 moles.

In a second aspect, the present invention provides a magnesium compound useful as a spheric carrier used in the preparation of a catalyst component for olefin polymerization, which magnesium compound has a characteristic DSC profile characterized by having a distinct exothermal peak in a temperature range of from 70 to 250° C., said exothermal peak having a peak maximum at a temperature of from 100 to 220° C. and an associated exothermal enthalpy of larger than 40 J/g.

In a preferred embodiment, the DSC profile of the magnesium compound is characterized in that the peak maximum of the exothermal peak appears at a temperature of from 100 to 200° C.

In another preferred embodiment, the DSC profile of the magnesium compound is characterized in that the peak maximum of the exothermal peak appears at a temperature of from 130 to 210° C.

In still another preferred embodiment, the DSC profile of the magnesium compound is characterized in that the peak maximum of the exothermal peak appears at a temperature of from 130 to 200° C.

In a preferred embodiment, the DSC profile of the magnesium compound is characterized in that the exothermal peak has an associated exothermal enthalpy of larger than 100 J/g.

In a third aspect, the present invention provides a magnesium compound useful as a spheric carrier used in the preparation of a catalyst component for olefin polymerization, which magnesium compound has a characteristic X-ray diffraction pattern characterized in that in a 2θ angle range of from 5° to 15°, there are at least two diffraction lines, wherein the intensest diffraction line appears at a diffraction angle 2θ of 10.0±0.4°, and the secondary intensest diffraction line appears at a diffraction angle 2θ of from 10.5 to 12.5°, for example at a diffraction angle 2θ of 11.5±0.4°, and has an intensity of at least 0.2 times the intensity of the intensest diffraction line.

In an embodiment, the X-ray diffraction pattern of the magnesium compound is further characterized in that diffraction lines appeared in the 2θ angle range of from 5° to 15° other than the intensest and the secondary intensest diffraction lines have intensities of less than 0.2 times the intensity of the intensest diffraction line.

In an embodiment, the X-ray diffraction pattern of the magnesium compound is further characterized in that in a 2θ angle range of from 15 to 32°, there is a broad diffraction peak with a peak maximum in a 2θ angle range of from 20 to 21°.

In another embodiment, the X-ray diffraction pattern of the magnesium compound is further characterized in that in a 2θ angle range of from 15 to 32°, there is a broad diffraction peak with a peak maximum in a 2θ angle range of from 20 to 21° and at least one shoulder peak at a 2θ angle of 16.5±0.4° and/or 25.6±0.4°.

Without being limited to any specific theory, it is believed that the magnesium compound of the invention prepared from the $MgX_2$, the $R_1OH$ and the epoxy compound of the formula (I) has a formula:

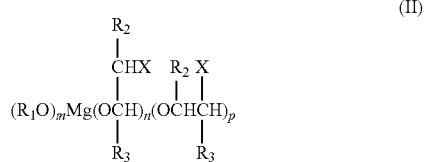

wherein p+m+n=2.

Taking a magnesium compound prepared from magnesium dichloride, epoxy chloropropane, and ethanol as an example, it is possible that the magnesium compound is formed through the following reaction mechanism:

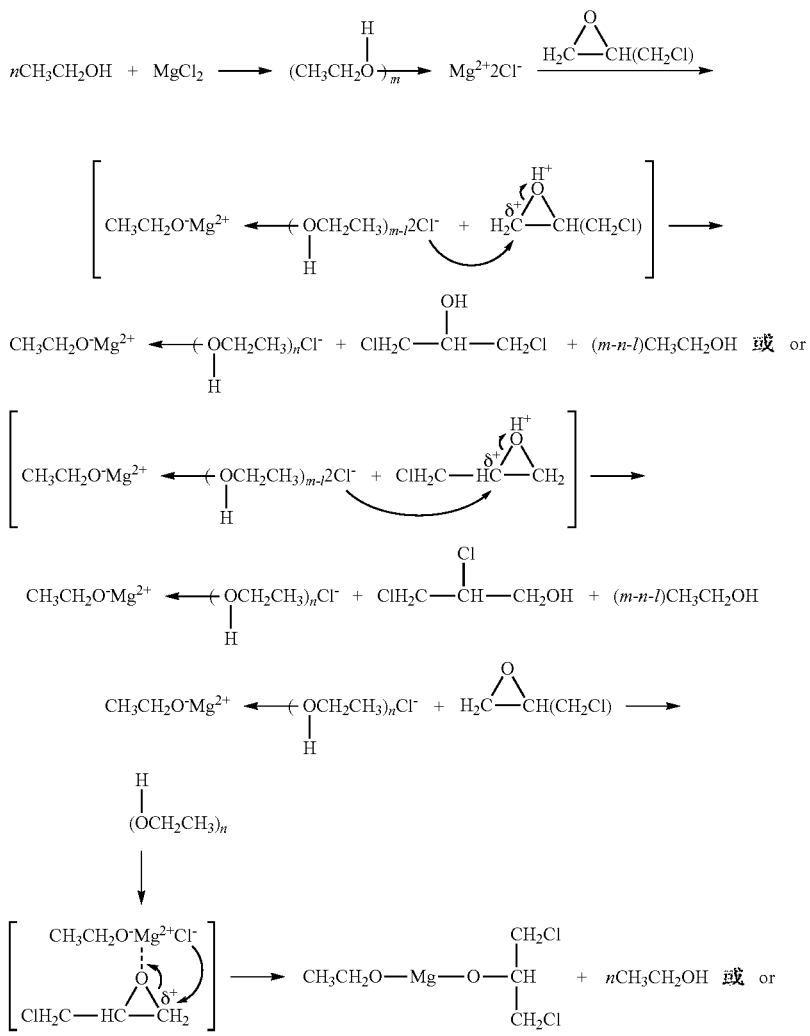

-continued

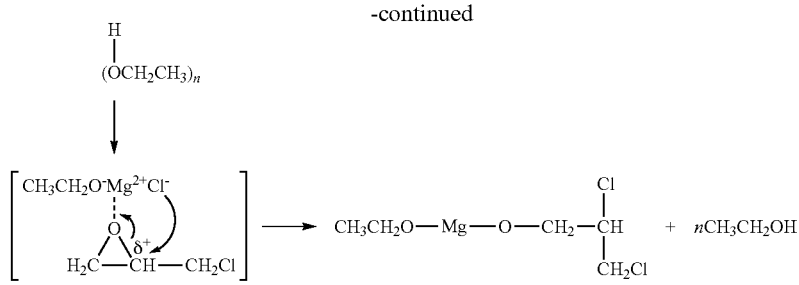

In a fourth aspect, the present invention provides a process for preparing the spheric magnesium compound of the invention, the process comprising a) mixing a magnesium halide of a general formula of $MgX_{2-n}R_n$, an alcohol compound and an optional inert liquid medium in a vessel, preferably in a closed vessel, heating the resultant mixture to a temperature of from 30 to 160° C. and allowing it to react, to form a magnesium halide-alcohol adduct solution; and b) reacting the magnesium halide-alcohol adduct solution with an epoxy compound of the general formula (I):

(I)

at a temperature of from 30 to 160° C., to form a particulate spheric magnesium compound, wherein R, X, $R_2$ and $R_3$ are as defined above.

In the above process, relative to one mole of the magnesium halide, the amount of the alcohol used may range from 4 to 40 moles, preferably from 4 to 30 moles, more preferably from 6 to 25 moles, and still more preferably from 6 to 20 moles, and the amount of the epoxy compound used may range from 1 to 10 moles, and preferably from 2 to 6 moles.

The inert liquid medium may be chosen from liquid aliphatic, aromatic or alicyclic hydrocarbons, silicone oils, and mixtures thereof. Examples include, but are not limited to, hexanes, heptanes, octanes, nonanes, decanes, dodecanes, kerosenes, paraffin oils, vaseline oils, white oils, methylsilicone oils, and mixtures thereof. If the inert liquid medium is used, there is not a specific limitation to the amount thereof. However, it is preferred that the inert liquid medium is used in an amount of from ⅓ to 20 L, and preferably from ⅔ to 10 L, relative to one mole of the magnesium halide.

Examples and preferences of the magnesium halide, the alcohol compound and the epoxy compound are as described above for the first aspect.

In the above process, a trace amount of water present in the magnesium halide and/or the alcohol can be involved in the reaction to form the magnesium halide-alcohol adduct solution.

In step a) of the above process, the individual materials may be added into the vessel in any order.

The particulate spheric magnesium compound formed in step b) of the above process may be washed with an inert hydrocarbon solvent such as hexane and then dried (for example, dried under reduced pressure), as well known by those skilled in the art.

In an embodiment, the preparation process may be carried out as follows:

1) the magnesium halide-alcohol adduct solution is prepared by heating a mixture of the magnesium halide, the alcohol and the optional inert liquid medium in a closed vessel with stirring to a temperature of from 30 to 160° C., and preferably from 60 to 120° C., and allowing the mixture to react sufficiently; and 2) the particulate spheric magnesium compound is formed by adding the epoxy compound into the magnesium halide-alcohol adduct solution while stirring and allowing the resultant mixture to react at a temperature of from 30 to 160° C., and preferably from 60 to 120° C.

In another embodiment, the preparation process may be carried out as follows:

1) the magnesium halide-alcohol adduct solution is prepared by heating a mixture of the magnesium halide, the alcohol and the optional inert liquid medium in a closed vessel with stirring to a temperature of from 30 to 160° C., and preferably from 60 to 120° C., and allowing the mixture to react sufficiently; and 2) the particulate spheric magnesium compound is formed by adding the magnesium halide-alcohol adduct solution into a mixture of the epoxy compound and the inert liquid medium and allowing the resultant mixture to react at a temperature of from 30 to 160° C., and preferably from 60 to 120° C.

The total amount of the inert liquid medium used in steps 1) and 2) ranges from ⅓ to 20 L, and preferably from ⅔ to 10 L, relative to one mole of the magnesium halide. The inert liquid medium may be distributed at any suitable ratio between steps 1) and 2). For example, the ratio of the inert liquid medium used in step 1) to that used in step 2) may range from 1:10-5:1.

In another embodiment, the preparation process may be carried out as follows:

1) the magnesium halide-alcohol adduct solution is formed by reacting the magnesium halide with the alcohol in the inert liquid medium in a closed vessel at a temperature below 60° C. with stirring; and 2) the particulate spheric magnesium compound is formed by adding the epoxy compound into the magnesium halide-alcohol adduct solution, heating the resultant mixture with stirring to a temperature of from 60 to 160° C., and preferably from 60 to 120° C., and allowing the mixture to react sufficiently.

In this embodiment, the amount of the alcohol used ranges preferably from 10 to 30 moles, and more preferably from 15 to 25 moles, relative to one mole of the magnesium halide.

The spheric magnesium compound of the invention is useful as a spheric carrier used in the preparation of a catalyst component for olefin polymerization. Thus, in a fifth aspect, the present invention provides use of the spheric magnesium compound as a carrier in the preparation of a catalyst component for olefin polymerization.

According to the use of the invention, a catalyst component for olefin polymerization is formed by contacting the particulate spheric magnesium compound with a titanium compound and an optional internal electron donor compound. This can be performed according to a process known per se, such as the process described in Chinese patent CN1091748A.

The titanium compound and optional internal electron donor compound used in the preparation of a catalyst component for olefin polymerization as well as their amounts are well known by those skilled in the art.

In an embodiment, the catalyst component is prepared by a process comprising the steps of: suspending the particulate spheric magnesium compound in chilled titanium tetrachloride or a mixture of titanium tetrachloride and an inert solvent, with the temperature of the liquid being generally in a range of from −30° C. to 0° C., and preferably from −20° C. to −10° C.; heating the resulting mixture to a temperature of from 40° C. to 130° C., and preferably from 80° C. to 130° C., and maintaining at that temperature for 0.5 to 2.0 hours; then recovering the solids by filtration; optionally, repeating the above treatment with titanium tetrachloride one or more times, and preferably 1 to 4 times; and finally, washing the resultant solid catalyst component with an inert solvent several times, for example, 2 to 5 times. The inert solvent is preferably an aliphatic or aromatic hydrocarbon, such as hexane, heptane, octane, decane, toluene, and the like.

Before, during or after the reaction between the particulate spheric magnesium compound and the titanium compound, at least one internal electron donor compound may be used to treat the particulate spheric magnesium compound. In particular, when the catalyst component is one intended to use in propylene polymerization, the addition of such an internal electron donor compound may be crucial in order to obtain a propylene polymer with a high isotacticity.

In the above process, relative to one mole of magnesium in the spheric magnesium compound, the amount of the internal electron donor compound used may range from 0 to 0.5 moles, and preferably from 0.05 to 0.3 moles; and the amount of the titanium compound used may range from 5 to 50 moles, and preferably from 8 to 30 moles.

When used in olefin polymerization, in particular in propylene (co)polymerization, the solid catalyst component prepared by using the magnesium compound of the invention as a carrier achieves at least one of the following desired effects: high polymerization activity of catalyst, high stereospecificity of catalyst, good hydrogen response of catalyst, high stereoregularity of polymer having high melt index, and low content of polymer fines.

EXAMPLES

The following examples are provided to further illustrate the present invention and by no means intend to limit the scope thereof.

Testing Methods:

1. Melt index of polymers: measured according to ASTM D1238-99, at 230° C. and 2.16 kg load.

2. Isotacticity of polymers: measured by heptane extraction method carried out as follows: 2 g of dry polymer sample was extracted with boiling heptane in an extractor for 6 hours, then the residual substance was dried to constant weight, and the ratio of the weight of the residual polymer (g) to 2 (g) was regarded as isotacticity.

3. Particle size distribution: average particle size and particle size distribution of the particulate magnesium halide adducts were measured on Masters Sizer Model 2000 (manufactured by Malvern Instruments Co., Ltd.).

4. DSC profile: acquired on a DSC 7 instrument available from Perkin Elmer Co. by raising the temperature from 25 to 300° C. at a rate of 10° C./min under nitrogen atmosphere.

5. X-ray diffraction pattern: acquired on an X'Pert MPD Model multifunctional X-ray diffractometer with a graphite monochromator and a scintillation counter available from Philips Co., Netherlands, under the following conditions: CuKα (λ=1.5406 Å), tube voltage of 40 kV, tube current of 40 mA, DS=SS=1° slot system, receiving slot of 0.3 mm, scanning speed of 3° (2θ)/min., and scanning range (2θ) of from 5° to 75°. The sample was sealed in a 50 micron-thickness polyethylene plastic bag.

Example 1

A. Preparation of Spheric Magnesium Compound

To a 500 ml reactor were charged successively 7.2 g of magnesium dichloride, 180 ml of white oil and 82 ml of ethanol, and the contents were heated with stirring to 90° C. After the contents were allowed to react at that temperature for 1 hour, 24 ml of epoxy chloropropane was added to the reactor, and the reaction was allowed to continue at that temperature for 0.5 hours. After removing the liquid by filtration, the residual solids were washed with hexane five 5 times and then dried under vacuum, to give a spheric magnesium compound.

A DSC profile of the spheric magnesium compound is shown in FIG. 1.

Figure 3:
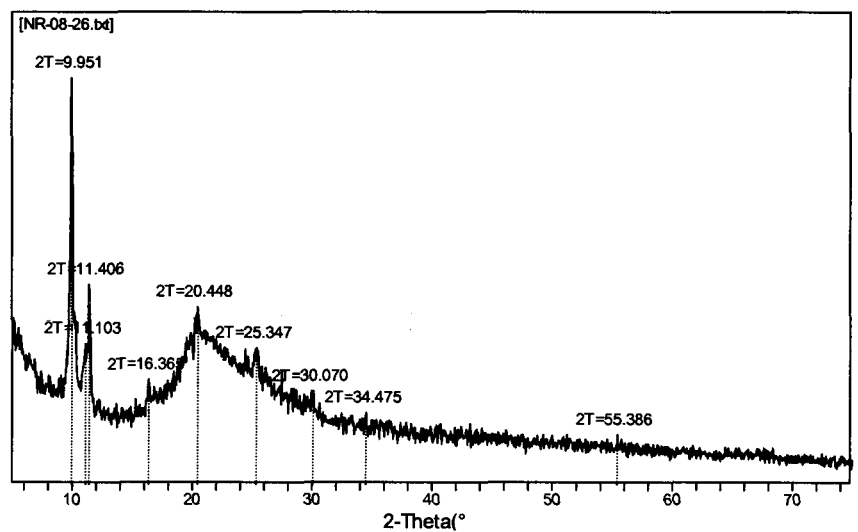
FIG. 3 shows an X-ray diffraction pattern of the magnesium compound carrier prepared in Example 1.

An X-ray diffraction pattern of the spheric magnesium compound is shown in FIG. 3. In this X-ray diffraction pattern, in the 2θ angle range of from 5 to 15°, there are three diffraction lines at 2θ angles of 9.95° (100%), 11.1° (15.7%) and 11.41° (36%), and in the 2θ angle range of from 15 to 32°, there is a broad peak with a peak maximum at 2θ angle of 20.45° (11.3%) and shoulder peaks at 2θ angles of 16.37° (7.7%), 25.35° (7.7%) and 30.07° (7.1%). The numerical values in the parentheses represent intensities relative to the intensest diffraction line $I/I_0$).

Figure 2:
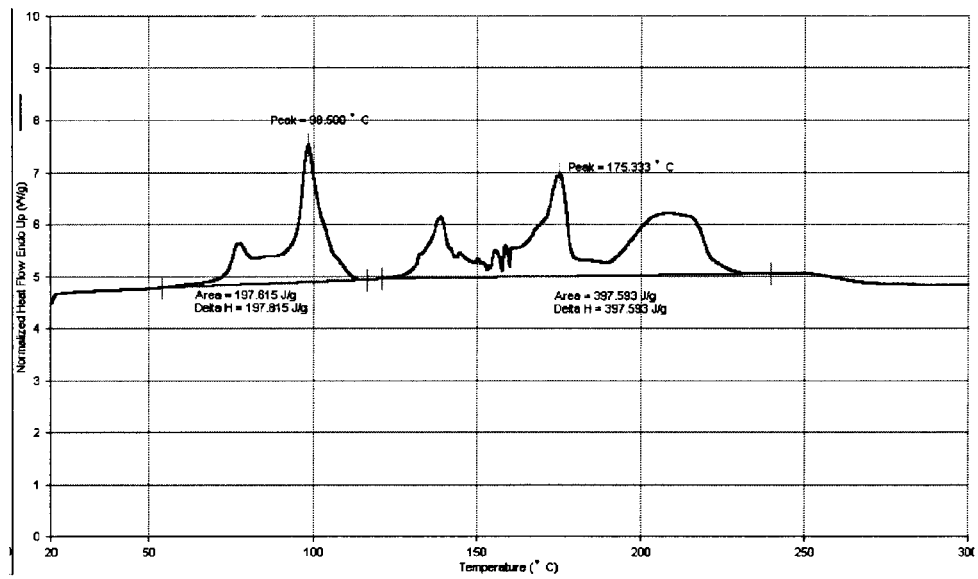
FIG. 2 shows a DSC profile of a known magnesium dichloride-ethanol adduct of formula $MgCl_2 \cdot 2.7C_2H_5OH$.
Figure 4:
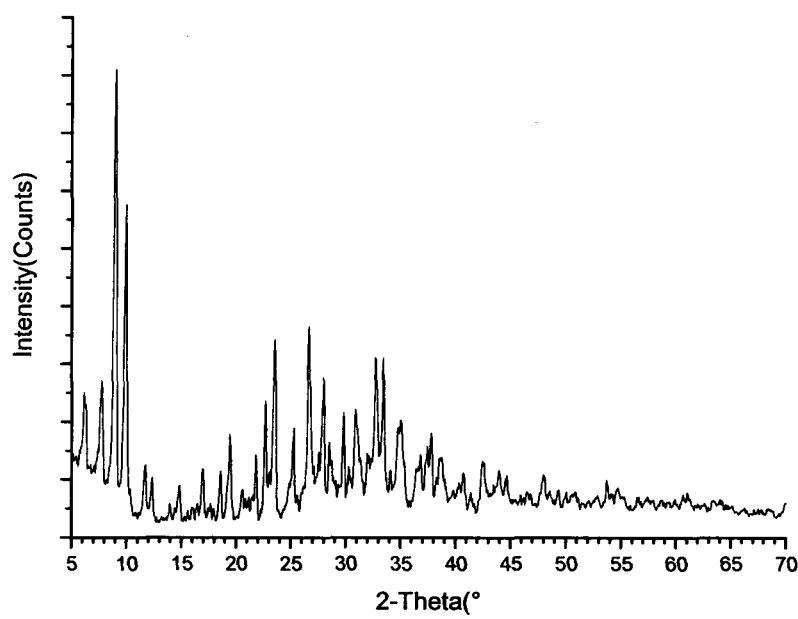
FIG. 4 shows an X-ray diffraction pattern of the known magnesium dichloride-ethanol adduct of formula $MgCl_2 \cdot 2.7C_2H_5OH$.
Figure 5:
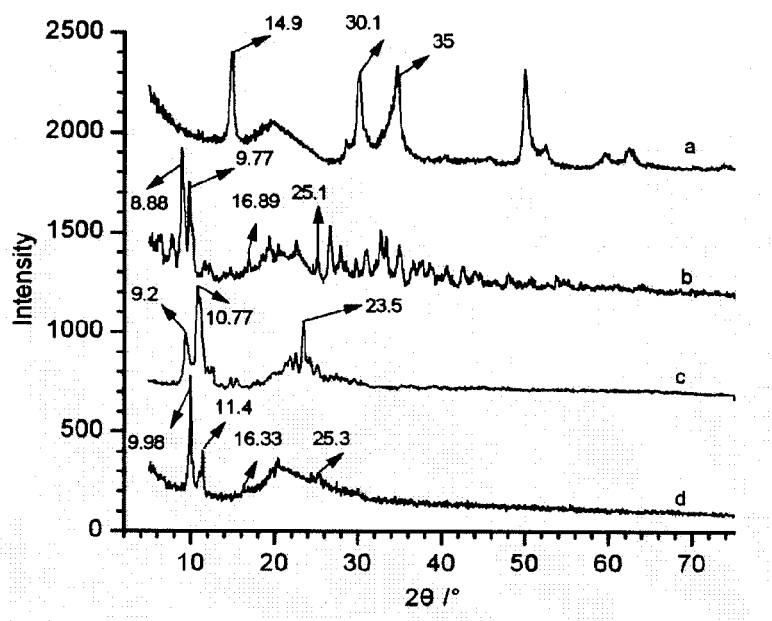
FIG. 5 shows X-ray diffraction patterns of several carriers, wherein a is one for $MgCl_2$; b is one for $MgCl_2 \cdot 2.7C_2H_5OH$; c is one for diethoxy magnesium; and d is one for the magnesium compound carrier of the invention.
Figure 6:
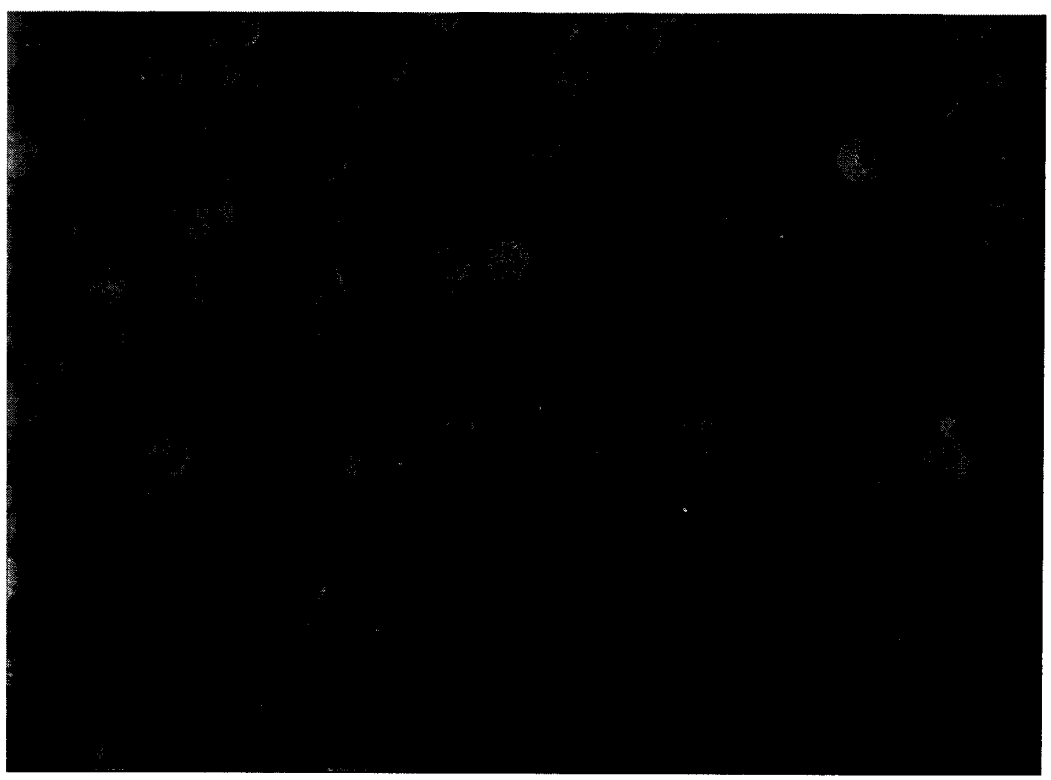
FIG. 6 shows a micrograph of the magnesium compound carrier prepared in Example 1.

FIG. 2 shows a DSC profile of a known magnesium dichloride-ethanol adduct of formula $MgCl_2 \cdot 2.7C_2H_5OH$, and FIG. 4 shows an X-ray diffraction pattern of this magnesium dichloride-ethanol adduct. FIG. 5 further shows X-ray diffraction patterns of several carriers, wherein a is one for $MgCl_2$; b is one for $MgCl_2 \cdot 2.7C_2H_5OH$; c is one for diethoxy magnesium; and d is one for the present carrier. By comparing said DSC profiles and X-ray diffraction patterns, it is apparent that the magnesium compound carrier of the invention is different from the magnesium dichloride-ethanol adduct carrier and the magnesium dichloride carrier known in the art.

B. Preparation of Spheric Catalyst Component 100 ml of titanium tetrachloride was added to a 300 ml glass reactor and cooled to −20° C. Then 8 g of the above-prepared spheric magnesium compound was added to the reactor, and the contents were heated to 110° C., with 1.5 ml of diisobutyl phthalate being added to the reactor during the heating. After the liquid was removed through filtration, the residual solids were wished with titanium tetrachloride twice and with hexane thrice, and then dried under vacuum to give a spheric catalyst component.

C. Propylene Polymerization

Under nitrogen atmosphere, to a 5 L stainless steel autoclave were charged successively 2.5 L of propylene, 1mmol of triethyl aluminum in 10 ml of hexane, 0.05 mmol of methyl cyclohexyl dimethoxy silane (CHMMS) in 1 ml of hexane, 10 mg of the above-prepared catalyst component and 1.5 L (standard volume) of hydrogen gas. The contents were heated to 70° C., and polymerization was allowed to continue at 70° C.

for 1 hour. The autoclave was cooled and then the pressure was vented. The autoclave was opened and the resulting propylene polymer was recovered. The results are shown in Table 2 below.

Example 2

A spheric magnesium compound was prepared according to the procedure described in Example 1, step A, except that the reaction temperature was 100° C.

A DSC profile of the spheric magnesium compound has an exothermal peak at a temperature range of from 75.6 to 249° C., said exothermal peak having a peak maximum at 161.5° C. and an associated exothermal enthalpy of 304.2 J/g.

The spheric magnesium compound has an X-ray diffraction pattern, wherein in the 2θ angle range of from 5 to 15°, there are two diffraction lines at 2θ angles of 10.1° (100%) and 11.59° (39.3%), and in the 2θ angle range of from 15 to 32°, there is a broad peak with a peak maximum at 2θ angle of 20.2° (43.5%) and shoulder peaks at 2° angles of 16.46° (9.5%), 25.40° (11%), 27.43 (7.3%) and 30.17° (9.1%). The numerical values in the parentheses represent intensities relative to the intensest diffraction line ($I/I_0$).

Preparation of spheric catalyst component and propylene polymerization were conducted according to the procedures described in Example 1.

Example 3

To a 500 ml reactor were charged successively 10.5 g of magnesium dichloride, 180 ml of white oil and 120 ml of ethanol, and the contents were heated with stirring to 85° C. After the contents were allowed to react at that temperature for 1 hour, 35 ml of epoxy chloropropane was added to the reactor, and the reaction was allowed to continue at that temperature for 0.5 hours. After removing the liquid by filtration, the residual solids were washed with hexane five 5 times and then dried under vacuum, to give a spheric magnesium compound.

A DSC profile of the spheric magnesium compound has an exothermal peak at a temperature range of from 77.87 to 209.83° C., said exothermal peak having a peak maximum at 151.37° C. and an associated exothermal enthalpy of 199.31 J/g.

The spheric magnesium compound has an X-ray diffraction pattern, wherein in the 2θ angle range of from 5 to 15°, there are two diffraction lines at 2θ angles of 10.05° (100%) and 11.55° (28.8%), and in the 2θ angle range of from 15 to 32°, there is a broad peak with a peak maximum at 2θ angle of 20.71° (13.1%) and shoulder peaks at 2θ angles of 16.36° (6.7%), 19.62 (6.3%), 25.40° (15%) and 30.0° (3.8%). The numerical values in the parentheses represent intensities relative to the intensest diffraction line ($I/I_0$).

Preparation of spheric catalyst component and propylene polymerization were conducted according to the procedures described in Example 1.

Example 4

To a 300 ml reactor were charged successively 4.8 g of magnesium dichloride, 100 ml of decane and 30 ml of ethanol, and the contents were heated with stirring to 75° C. After the contents were allowed to react at that temperature for 1 hour, 8 ml of epoxy chloropropane was added to the reactor, and the reaction was allowed to continue at that temperature for 1 hour. After removing the liquid by filtration, the residual solids were washed with hexane five 5 times and then dried under vacuum, to give a spheric magnesium compound.

Preparation of spheric catalyst component and propylene polymerization were conducted according to the procedures described in Example 1.

Example 5

To a 500 ml reactor were charged successively 24 g of magnesium dichloride, 150 ml of methyl silicone oil and 90 ml of ethanol, and the contents were heated with stirring to 100° C. After the contents were allowed to react at that temperature for 2 hours, the reaction mixture was transferred into an epoxy chloropropane/methyl silicone oil (40 ml/350 ml) mixture preheated to 100° C., and the reaction was allowed to continue for 1 hour. After removing the liquid by filtration, the residual solids were washed with hexane five 5 times and then dried under vacuum, to give a spheric magnesium compound.

A DSC profile of the spheric magnesium compound has an exothermal peak at a temperature range of from 95.6 to 178.7° C., said exothermal peak having a peak maximum at 137.67° C. and an associated exothermal enthalpy of 43.6 J/g.

Preparation of spheric catalyst component and propylene polymerization were conducted according to the procedures described in Example 1.

Example 6

To a 300 ml reactor were charged successively 4.8 g of magnesium dichloride, 150 ml of decane and 54 ml of ethanol, and the contents were heated with stirring to 55° C. After the contents were allowed to react at that temperature for 1 hour, 8 ml of epoxy chloropropane was added to the reactor, and the reaction mixture was then heated to 80° C. and allowed to react for 0.5 hours. After removing the liquid by filtration, the residual solids were washed with hexane five 5 times and then dried under vacuum, to give a spheric magnesium compound.

A DSC profile of the spheric magnesium compound has an exothermal peak at a temperature range of from 90.2 to 192.7° C., said exothermal peak having a peak maximum at 137.2° C. and an associated exothermal enthalpy of 102.5 J/g.

The spheric magnesium compound has an X-ray diffraction pattern, wherein in the 2θ angle range of from 5 to 15°, there are two diffraction lines at 2θ angles of 10.14° (100%) and 11.55° (31.9%), and in the 2θ angle range of from 15 to 32°, there is a broad peak with a peak maximum at 2θ angle of 20.41° (53.3%) and shoulder peaks at 2θ angles of 16.72° (11.4%), 25.44° (16.3%) and 30.15° (13.3%). The numerical values in the parentheses represent intensities relative to the intensest diffraction line ($I/I_0$).

Preparation of spheric catalyst component and propylene polymerization were conducted according to the procedures described in Example 1.

Example 7

To a 500 ml reactor were charged successively 7.2 g of magnesium dichloride, 180 ml of white oil, 20 ml of 2-ethylhexanol and 70 ml of ethanol, and the contents were heated with stirring to 90° C. After the contents were allowed to react at that temperature for 1 hour, 20 ml of epoxy chloropropane was added to the reactor, and the reaction was allowed to continue at that temperature for 0.5 hours. After removing the liquid by filtration, the residual solids were washed with hexane five 5 times and then dried under vacuum, to give a spheric magnesium compound.

A DSC profile of the spheric magnesium compound has an exothermal peak at a temperature range of from 73.2 to 229.3° C., said exothermal peak having a peak maximum at 180.67° C. and an associated exothermal enthalpy of 420.4 J/g.

The spheric magnesium compound has an X-ray diffraction pattern, wherein in the 2θ angle range of from 5 to 15°, there are three diffraction lines at 2θ angles of 10.0° (100%), 11.0° (17.5%) and 11.45° (23.4%), and in the 2θ angle range of from 15 to 32°, there is a broad peak with a peak maximum at 2θ angle of 20.8° (21.3%) and shoulder peaks at 2θ angles of 16.26° (5.3%), 25.3° (4.2%) and 26.4° (6.1%). The numerical values in the parentheses represent intensities relative to the intensest diffraction line ($I/I_0$).

Preparation of spheric catalyst component and propylene polymerization were conducted according to the procedures described in Example 1.

Example 8

To a 300 ml reactor were charged successively 4.8 g of magnesium dichloride, 100 ml of decane and 30 ml of ethanol, and the contents were heated with stirring to 80° C. After the contents were allowed to react at that temperature for 1 hour, 7 ml of epoxy propane was added to the reactor, and the reaction was allowed to continue at that temperature for 1 hour. After removing the liquid by filtration, the residual solids were washed with hexane five 5 times and then dried under vacuum, to give a spheric magnesium compound.

A DSC profile of the spheric magnesium compound has an exothermal peak at a temperature range of from 57.5 to 236.4° C., said exothermal peak having a peak maximum at 198.37° C. and an associated exothermal enthalpy of 265.7 J/g.

Preparation of spheric catalyst component and propylene polymerization were conducted according to the procedures described in Example 1.

Example 9

In a 500 ml reactor, a spheric magnesium compound carrier was prepared according to the procedure of Example 1. At the end of the last times of hexane washing, the liquid was removed by filtration. To the reactor was directly added 120 ml of titanium tetrachloride cooled to −20° C., and the contents were then heated to 110° C. while stirring, with 2 ml of diisobutyl phthalate being added to the reactor during the heating. After the liquid was removed through filtration, the residual solids were wished with titanium tetrachloride twice and with hexane thrice, and then dried under vacuum to give a spheric catalyst component. The obtained catalyst component has an average particle size (D50) of 60.6 microns and a particle size distribution, SPAN ((D90−D10)/D50), of 0.54.

Example 10

To a 500 ml reactor were charged successively 7.2 g of magnesium dichloride, 180 ml of white oil and 82 ml of ethanol, and the contents were heated with stirring to 95° C. After the contents were allowed to react at that temperature for 1 hour, 30 ml of epoxy chloropropane was added to the reactor, and the reaction was allowed to continue at that temperature for 0.5 hours. After removing the liquid by filtration, the residual solids were washed with hexane five 5 times and then dried under vacuum, to give a spheric magnesium compound.

The spheric magnesium compound has an X-ray diffraction pattern, wherein in the 2θ angle range of from 5 to 15°, there are two diffraction lines at 2θ angles of 9.8° (100%) and 10.7° (50%), and in the 2θ angle range of from 15 to 32°, there is a broad peak with a peak maximum at 2θ angle of 20.3° (24%) and shoulder peaks at 2θ angles of 16.6° (12.2%), 25.9° (8.0%), 27.1° (5.2%), 27.86° (5.2%), and 29.85° (11.8%). The numerical values in the parentheses represent intensities relative to the intensest diffraction line ($I/I_0$).

TABLE 1

Particle size distribution of magnesium compounds

| Example No. | Particle size distribution of spheric magnesium compounds | | | |
|---|---|---|---|---|
| | D10 μm | D50 μm | D90 μm | Particle size distribution SPAN |
| Example 1 | 58.5 | 79.0 | 128.8 | 0.9 |
| Example 2 | 62.4 | 91.5 | 117.2 | 0.6 |
| Example 3 | 75.2 | 87.5 | 136.5 | 0.7 |
| Example 4 | 152.3 | 215.0 | 281.3 | 0.6 |
| Example 5 | 14.4 | 28.5 | 61.9 | 1.6 |
| Example 6 | 25.7 | 95.5 | 162.3 | 1.4 |
| Example 7 | 39.0 | 72.4 | 108.5 | 1.0 |
| Example 8 | 124.5 | 149.1 | 201.3 | 0.6 |
| Example 10 | — | 99.7 | — | 0.76 |

It can be seen from the results shown in Table 1 that the spheric magnesium compound carriers of the invention have narrow particle size distribution.

TABLE 2

Catalyst performance

| Example No. | Polymerization activity (KgPP/gCat.) | Isotacticity index of polymer (wt %) | Polymer melt index (g/10 min) |
|---|---|---|---|
| Example 1 | 37.8 | 97.3 | 12 |
| Example 3 | 34.6 | 96.8 | 8.1 |
| Example 4 | 40.2 | 98.0 | 5.6 |
| Example 5 | 19.8 | 97.3 | 7.7 |
| Example 7 | 51.3 | 97.7 | 6.0 |
| Example 8 | 42.8 | 97.6 | 4.8 |
| Example 9 | 41.6 | 97.6 | 8.0 |

It can be seen from the results shown in Table 2 that, when used in propylene polymerization, the catalysts prepared by using the spheric magnesium compounds of the invention as a carrier exhibit high polymerization activities and high stereospecificities.

The patents, patent applications and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:

1. A particulate spheric magnesium-containing carrier comprising solid particles directly formed in the reaction of at least the following components:
    (a) a magnesium halide represented by a general formula of $MgX_{2-n}R_n$, wherein X is independently chloride or bromide, R is a $C_1$-$C_{14}$ alkyl, a $C_6$-$C_{14}$ aryl, a $C_1$-$C_{14}$ alkoxy, or a $C_6$-$C_{14}$ aryloxy, and n is 0 or 1;
(b) an alcohol compound; and
(c) an epoxy compound represented by a general formula (I):

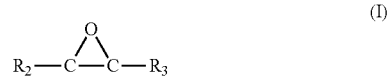

wherein $R_2$ and $R_3$ are independently hydrogen, a $C_1$-$C_5$ linear or branched alkyl, or a $C_1$-$C_5$ linear or branched haloalkyl.

2. The magnesium-containing carrier of claim 1, wherein the alcohol compound is at least one represented by a general formula of $R_1OH$, wherein $R_1$ is a $C_1$-$C_{12}$ alkyl, a $C_3$-$C_{10}$ cycloalkyl, a $C_7$-$C_{12}$ aralkyl or a $C_6$-$C_{10}$ aryl.

3. The magnesium-containing carrier of claim 2, wherein $R_1$ is a $C_1$-$C_8$ alkyl.

4. The magnesium-containing carrier of claim 1, wherein the magnesium halide is magnesium dichloride.

5. The magnesium-containing carrier of claim 1, wherein $R_2$ and $R_3$, which are the same or different, represent hydrogen, a $C_1$-$C_3$ alkyl or a $C_1$-$C_3$ haloalkyl.

6. The magnesium-containing carrier of claim 1, wherein in the formation of the magnesium compound, the amount of the component (2) used ranges from 4 to 40 moles, and the amount of the component (3) used ranges from 1 to 10 moles, relative to one mole of the magnesium halide.

7. The magnesium-containing carrier of claim 6, wherein the amount of the component (2) used ranges from 6 to 20 moles, and the amount of the component (3) used ranges from 2 to 6 moles, relative to one mole of the magnesium halide.

8. The magnesium-containing carrier of claim 1, which has a characteristic X-ray diffraction pattern characterized in that in a 2θ angle range of from 5° to 15°, there are at least two diffraction lines, wherein the intensest diffraction line appears at a diffraction angle 2θ of 10.0±0.4°, and the secondary intensest diffraction line appears at a diffraction angle 2θ of from 10.5 to 12.5°, and has an intensity of at least 0.2 times the intensity of the intensest diffraction line.

9. The magnesium-containing carrier of claim 8, wherein the X-ray diffraction pattern of the magnesium compound is further characterized in that diffraction lines appeared in the 2θ angle range of from 5° to 15° other than the intensest and the secondary intensest diffraction lines have intensities of less than 0.2 times the intensity of the intensest diffraction line.

10. The magnesium-containing carrier of claim 8, wherein the X-ray diffraction pattern of the magnesium compound is further characterized in that in a 2θ angle range of from 15 to 32°, there is a broad diffraction peak with a peak maximum in a 2θ angle range of from 20 to 21°.

11. The magnesium-containing carrier of claim 8, wherein the X-ray diffraction pattern of the magnesium compound is further characterized in that in a 2θ angle range of from 15 to 32°, there is a broad diffraction peak with a peak maximum in a 2θ angle range of from 20 to 21° and at least one shoulder peak at a 2θ angle of 16.5±0.4° and/or 25.6±0.4°.

12. The magnesium-containing carrier of claim 8, wherein the secondary intensest diffraction line appears at a diffraction angle 2θ of 11.5±0.4°.

13. The magnesium-containing carrier of claim 1, which has a characteristic DSC profile characterized by having a distinct exothermal peak in a temperature range of from 70 to 250° C., said exothermal peak having a peak maximum at a temperature of from 100 to 220° C. and an associated exothermal enthalpy of larger than 40 J/g.

14. The magnesium-containing carrier of claim 13, wherein the DSC profile of the magnesium compound is characterized in that the peak maximum of the exothermal peak appears at a temperature of from 100 to 200° C.

15. The magnesium-containing carrier of claim 13, wherein the DSC profile of the magnesium compound is characterized in that the peak maximum of the exothermal peak appears at a temperature of from 130 to 210° C.

16. The magnesium-containing carrier of claim 13, wherein the DSC profile of the magnesium compound is characterized in that the peak maximum of the exothermal peak appears at a temperature of from 130 to 200° C.

17. The magnesium-containing carrier of claim 13, wherein the DSC profile of the magnesium compound is characterized in that the exothermal peak has an associated exothermal enthalpy of larger than 100 J/g.

18. A process for preparing a magnesium-containing carrier, comprising
a) mixing a magnesium halide of a general formula of $MgX_{2-n}R_n$, an alcohol compound and an optional inert liquid medium in a vessel, heating the resultant mixture to a temperature of from 30 to 160° C. and allowing it to react, to form a magnesium halide-alcohol adduct solution; and
b) reacting the magnesium halide-alcohol adduct solution with an epoxy compound of the general formula (I):

at a temperature of from 30 to 160° C., to form a particulate spheric magnesium-containing carrier,
wherein R, X, $R_2$ and $R_3$ are as defined in claim 1.

19. The process of claim 18, having at least one of the following features:
in step a), the vessel is a closed vessel;
the alcohol compound is at least one represented by a general formula of $R_1OH$, wherein $R_1$ is a $C_1$-$C_{12}$ alkyl, a $C_3$-$C_{10}$ cycloalkyl, a $C_7$-$C_{12}$ aralkyl or a $C_6$-$C_{10}$ aryl;
the magnesium halide is magnesium dichloride;
in the general formula (I), $R_2$ and $R_3$, which are the same or different, represent hydrogen, a $C_1$-$C_3$ alkyl or a $C_1$-$C_3$ haloalkyl;
the inert liquid medium is used in step a), and the amount thereof is from ⅓ L to 20 L, relative to one mole of the magnesium halide; and
the amount of the alcohol compound used ranges from 4 to 40 moles, and the amount of the epoxy compound used ranges from 1 to 10 moles, relative to one mole of the magnesium halide.

20. The process of claim 18, having at least one of the following features:
the inert liquid medium is used in step a), and the amount thereof is from ⅔ L to 10 L, relative to one mole of the magnesium halide; and
the amount of the alcohol compound used ranges from 6 to 20 moles, and the amount of the epoxy compound used ranges from 2 to 6 moles, relative to one mole of the magnesium halide.

* * * * *